(12) United States Patent
Windheuser et al.

(10) Patent No.: US 11,678,786 B2
(45) Date of Patent: Jun. 20, 2023

(54) DEVICE AND METHODS FOR INSPECTION AND TREATMENT OF HEMORRHOIDS

(71) Applicant: Boston Scientific Scimed, Inc., Maple Grove, MN (US)

(72) Inventors: Kevin Windheuser, Hopkinton, MA (US); Peter Tabur, Hollis, NH (US); Oscar R. Carrillo, Jr., Middletown, CT (US); Shaun Dennis Comee, Fiskdale, MA (US); Kevin L. Bagley, Natick, MA (US); Nestor Allan Ibanez, Brighton, MA (US); Michael McGovern, Boston, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 268 days.

(21) Appl. No.: 16/912,322

(22) Filed: Jun. 25, 2020

(65) Prior Publication Data
US 2021/0015354 A1      Jan. 21, 2021

Related U.S. Application Data

(60) Provisional application No. 62/874,710, filed on Jul. 16, 2019.

(51) Int. Cl.
*A61B 1/31* (2006.01)
*A61B 17/128* (2006.01)
(Continued)

(52) U.S. Cl.
CPC ...... *A61B 1/00066* (2013.01); *A61B 1/00094* (2013.01); *A61B 1/00147* (2013.01);
(Continued)

(58) Field of Classification Search
CPC ... A61B 1/31; A61B 1/00094; A61B 1/00147; A61B 17/128; A61B 2017/00561;
(Continued)

(56) References Cited

U.S. PATENT DOCUMENTS 5,741,273 A * 4/1998 O'Regan .......... A61B 17/12013
606/1
5,788,715 A * 8/1998 Watson, Jr. ...... A61B 17/12013
606/140

(Continued)

FOREIGN PATENT DOCUMENTS

EP      2 818 097      12/2014

*Primary Examiner* — Timothy J Neal
*Assistant Examiner* — Mitchell Brian Hoag
(74) *Attorney, Agent, or Firm* — Fay Kaplun & Marcin, LLP

(57) ABSTRACT

A device may include an elongated housing formed of an optically transparent material, the housing extending from a proximal end to a distal end and including a lateral wall extending from the proximal end to a distal tip of the housing, the housing defining a lumen extending into the housing from a proximal opening in the proximal end of the housing. The device also may include a first port extending through the lateral wall of the housing to open the lumen of the housing to an exterior of the housing, the first port being sized and shaped to receive therein a target portion of tissue to be inspected and/or treated.

16 Claims, 9 Drawing Sheets

(51) Int. Cl.
  *A61B 1/00* (2006.01)
  *A61B 1/06* (2006.01)
  *A61B 17/12* (2006.01)
  *A61B 17/34* (2006.01)
  *A61B 17/00* (2006.01)

(52) U.S. Cl.
  CPC .............. *A61B 1/0684* (2013.01); *A61B 1/31* (2013.01); *A61B 17/12013* (2013.01); *A61B 17/128* (2013.01); *A61B 2017/00424* (2013.01); *A61B 2017/00561* (2013.01); *A61B 2017/00907* (2013.01); *A61B 2017/12018* (2013.01); *A61B 2017/3452* (2013.01); *A61B 2217/005* (2013.01)

(58) Field of Classification Search
  CPC .. A61B 2017/12018; A61B 2017/3452; A61B 2217/005; A61B 1/015; A61B 17/12; A61B 2017/12004; A61B 17/12009–12013; A61B 17/12013; A61F 6/20; A61F 5/0093; A61F 2/0004
  See application file for complete search history.

(56) References Cited

U.S. PATENT DOCUMENTS

| | | | | |
|---|---|---|---|---|
| 6,102,271 A * | 8/2000 | Longo | .................. | A61B 17/115 227/19 |
| 6,142,931 A * | 11/2000 | Kaji | .................. | A61B 17/3421 600/105 |
| 6,142,933 A * | 11/2000 | Longo | ..................... | A61B 1/31 600/184 |
| 7,189,247 B1 * | 3/2007 | Zirps | .................. | A61B 1/00087 606/140 |
| 8,097,002 B2 | 1/2012 | Delaney | | |
| 8,715,166 B2 | 5/2014 | Piskun | | |
| 2002/0072757 A1 * | 6/2002 | Ahmed | ............ | A61B 17/12013 606/139 |
| 2006/0167473 A1 * | 7/2006 | Scheyer | ............. | A61B 1/00177 606/139 |
| 2006/0259041 A1 * | 11/2006 | Hoffman | ............ | A61B 1/00087 606/139 |
| 2008/0275306 A1 * | 11/2008 | Rebuffat | .................. | A61B 1/31 600/184 |
| 2010/0130857 A1 * | 5/2010 | Szinicz | .................... | A61B 8/12 600/235 |
| 2010/0280523 A1 * | 11/2010 | Chen | ..................... | A61M 29/00 606/110 |
| 2013/0172918 A1 * | 7/2013 | Smith | .................. | A61B 1/0008 606/170 |
| 2013/0226198 A1 * | 8/2013 | Kamler | ............ | A61B 17/12013 606/140 |
| 2013/0274766 A1 * | 10/2013 | Isaacson | ................ | A61B 17/00 606/1 |
| 2017/0112371 A1 | 4/2017 | McGown | | |
| 2018/0317923 A1 * | 11/2018 | Robbins | ........... | A61B 17/12013 |
| 2021/0007748 A1 * | 1/2021 | Saenz Villalobos | ........................ | A61B 17/12009 |
| 2021/0077115 A1 * | 3/2021 | Nguyenba | ........ | A61B 17/12009 |

* cited by examiner

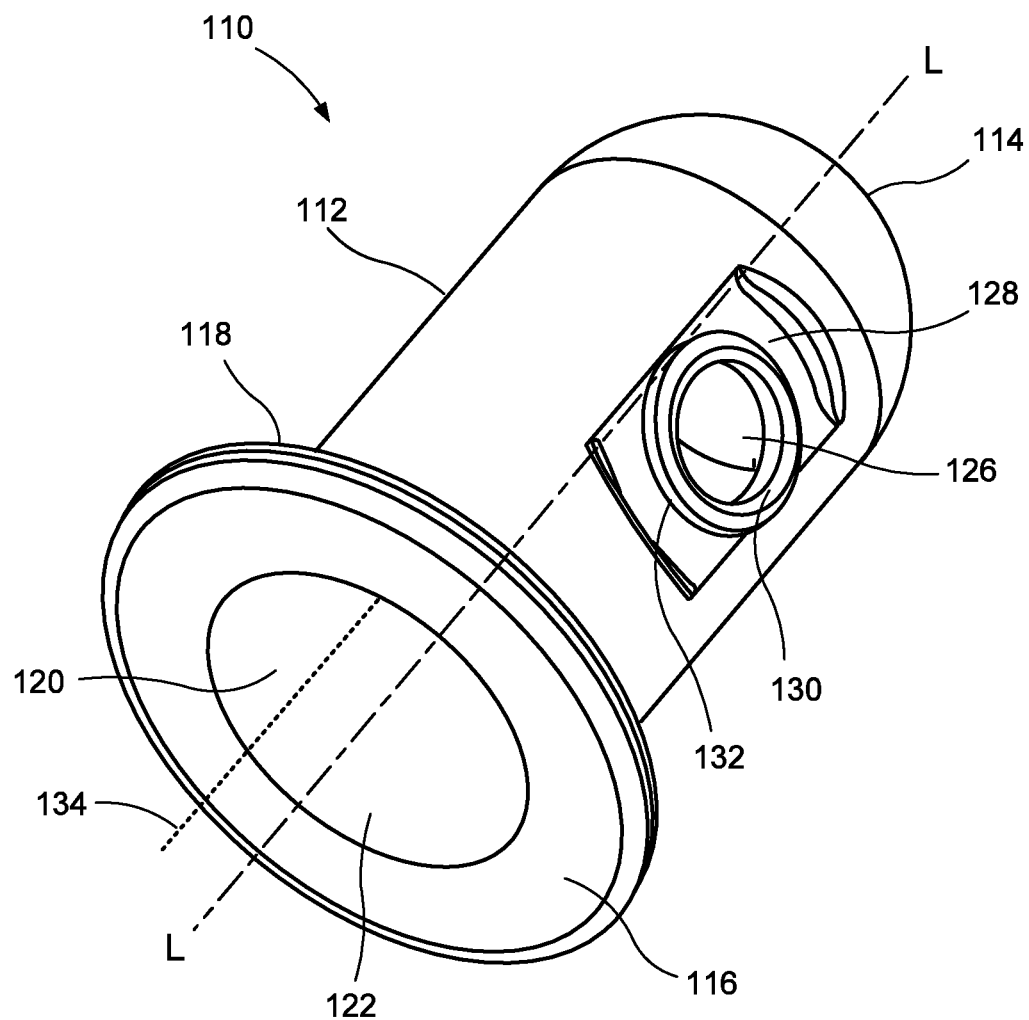
F I G. 2

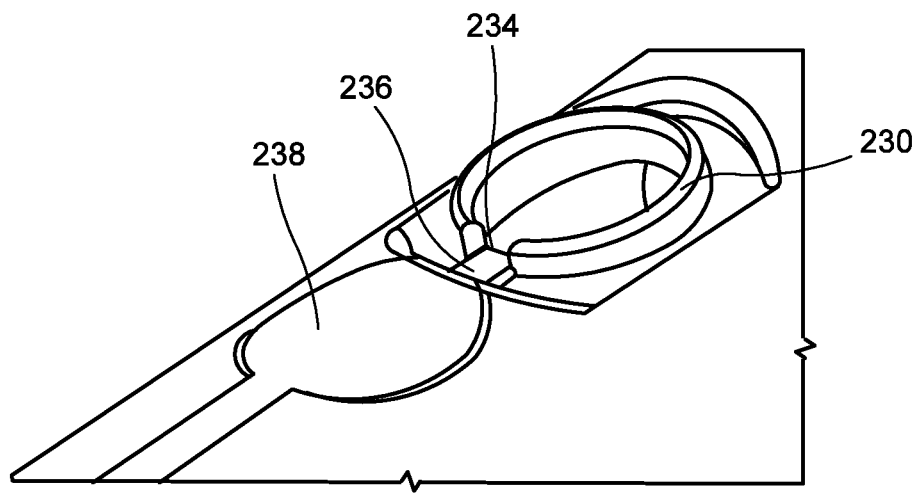
F I G. 6
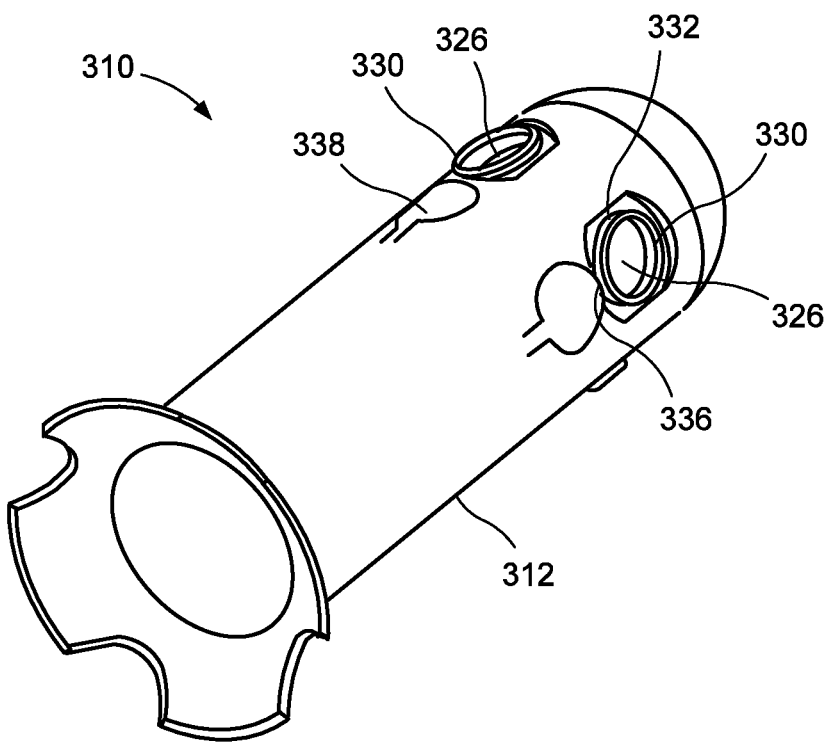
F I G. 7

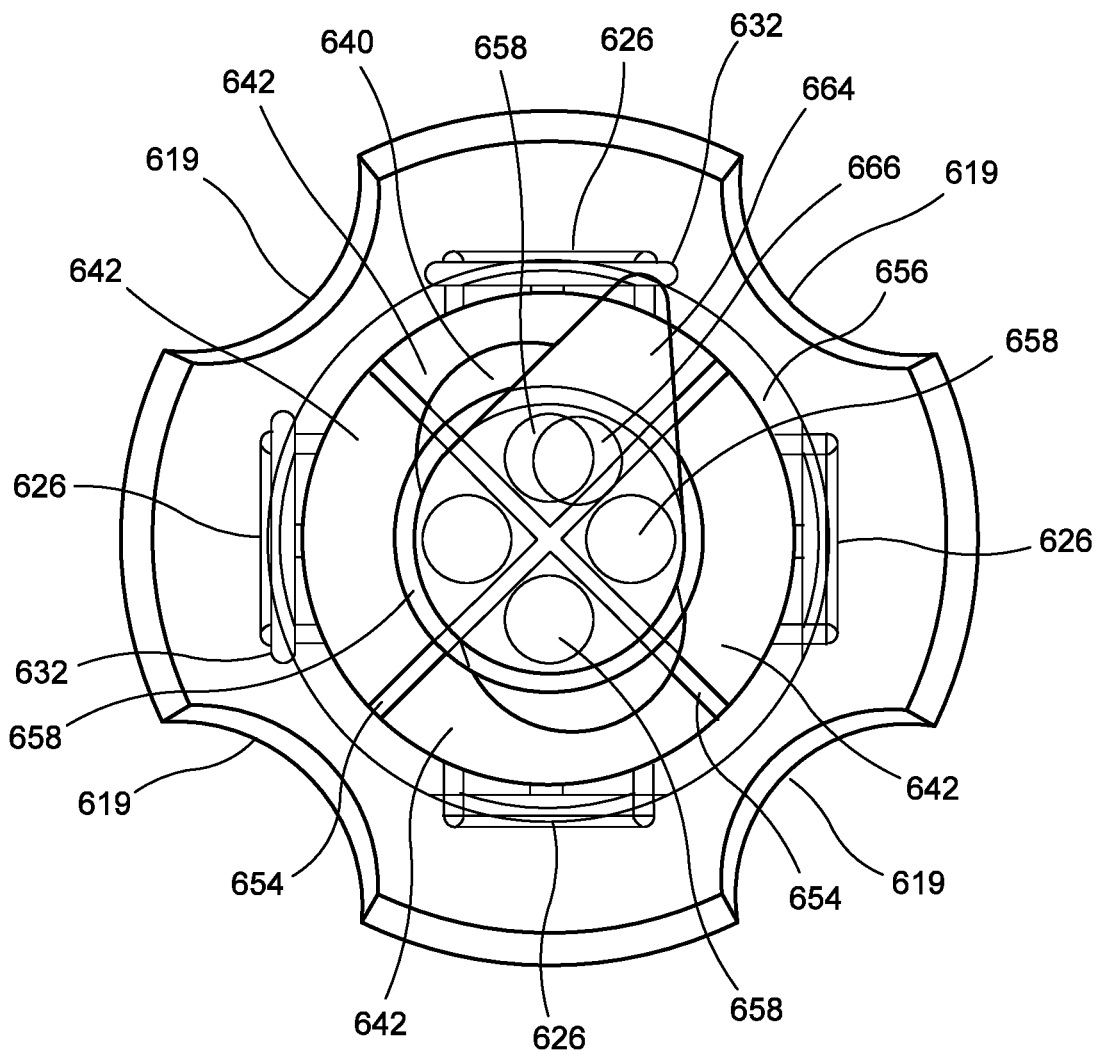
F I G. 11

DEVICE AND METHODS FOR INSPECTION AND TREATMENT OF HEMORRHOIDS

PRIORITY CLAIM

The present disclosure claims priority to U.S. Provisional Patent Application Ser. No. 62/874,710 filed Jul. 16, 2019; the disclosure of which is incorporated herewith by reference.

FIELD

The present disclosure relates generally to devices and methods for inspecting and/or treating hemorrhoids and, more specifically, for inspecting and/or treating internal hemorrhoids.

BACKGROUND

Hemorrhoids are swollen and inflamed veins around the anus or in the lower rectum. Hemorrhoids may be external, forming under the skin around the anus, or internal, forming in the lining of the anus and the lower rectum.

Internal hemorrhoids are often difficult to visually inspect and treat. Current scopes e.g. an anoscope allow for inspection, but are not equipped for treatment, while other tools are equipped for treatment but do not permit inspection and are inserted blind.

SUMMARY

The present disclosure relates to a device which includes an elongated housing formed of an optically transparent material, the housing extending from a proximal end to a distal end and including a lateral wall extending from the proximal end to a distal tip of the housing, the housing defining a lumen extending into the housing from a proximal opening in the proximal end of the housing; and a first port extending through the lateral wall of the housing to open the lumen of the housing to an exterior of the housing, the first port being sized and shaped to receive therein a target portion of tissue to be inspected and/or treated.

In an embodiment, the device further includes a first ligation band holding structure surrounding the first port, the first ligation band holding structure configured to stretch a first ligation band around the first port so that, tissue drawn into the lumen of the housing via the first port passes through the first ligation band; and a first ligation band deploying mechanism selectively operable to deploy the first ligation band from the first ligation band holding structure so that the first ligation band constricts around any tissue extending through the first port.

In an embodiment, the ligation band deployment mechanism includes a trigger line extending through the lumen of the housing through the port to releasably couple to the ligation band.

In an embodiment, the device further includes an eye through which the trigger line passes between the proximal end of the housing and the port, the eye being located within the lumen of the housing on a side of a longitudinal axis of the housing that is opposite the port.

In an embodiment, a portion of the trigger line between the port and the eye is separated into a plurality of filaments, the filaments engaging corresponding portions of the ligation band separated from one another around a circumference of the port.

In an embodiment, the housing is sized and shaped for insertion into a rectum and the port is sized and shaped to receive a hemorrhoid therein so that a user may view the hemorrhoid and tissue adjacent to the housing through the transparent housing via the proximal opening of the lumen of the housing.

In an embodiment, the ligation band deployment mechanism includes a tab formed as a part of the housing movable relative to adjacent portions of the housing, the tab being located adjacent to the port so that, the tab abuts a portion of a ligation band received around the port, movement of the tab relative to the adjacent portions of the housing moving the ligation band out of engagement with the ligation band holding structure.

In an embodiment, the device further includes a second port extending through the lateral wall of the housing to open the lumen of the housing to an exterior of the housing, the second port being sized and shaped to receive therein a target portion of tissue to be inspected and/or treated; a second ligation band holding structure surrounding the second port, the second ligation band holding structure configured to stretch a second ligation band around the second port so that, tissue drawn into the lumen of the housing via the second port passes through the second ligation band; and a second ligation band deploying mechanism selectively operable to deploy the second ligation band from the second ligation band holding structure so that the second ligation band constricts around any tissue extending through the second port.

In an embodiment, the device further includes a first vacuum chamber formed within the housing and in fluid communication with the first port; and a source of negative fluid pressure selectively couplable to the first vacuum chamber to apply suction to the first port to draw target tissue through the first port into the first vacuum chamber.

In an embodiment, the source of negative fluid pressure includes a plunger slidably mounted within the first vacuum chamber so that, drawing the plunger proximally through the first vacuum chamber draws negative pressure in the first vacuum chamber to apply suction to the first port.

In an embodiment, the device further includes a fluid conduit in fluid communication with the vacuum chamber, the fluid conduit extending proximally from the vacuum chamber to a proximal end including a coupling for attachment to the source of negative fluid pressure.

In an embodiment, the device further includes a first vacuum chamber formed within the housing and in fluid communication with the first port; a second vacuum chamber formed within the housing and in fluid communication with the second port; a source of negative fluid pressure selectively couplable to a selected one of the first and second vacuum chambers to apply suction to the corresponding one of the first and second ports to draw target tissue into the corresponding one of the first and second vacuum chambers.

In an embodiment, the device further includes a port selection mechanism that couples the source of negative pressure to the selected one of the vacuum chambers, the port selection mechanism including a sealing member that abuts a wall that seals the first and second vacuum chambers, the wall including a first hole opening the plunger chamber to the first vacuum port and a second hole opening the plunger chamber to the second vacuum chamber, the sealing member being movable between a first configuration in which the first opening is open and the second opening is sealed and a second configuration in which the second opening is open and the first opening is sealed. The source of negative fluid pressure includes a plunger slidably mounted within the first vacuum chamber so that, drawing the plunger proximally through the first vacuum chamber draws negative pressure in the first vacuum chamber to apply suction to the first port.

In an embodiment, the device further includes a radially protruding lip at the proximal end of the housing, extending along a surface that forms a portion of a sphere abutting the proximal end of the housing, wherein the lip has a diameter greater than that of the housing.

In an embodiment, the lip has a plurality of finger grips, the finger grips being concave cuts extending from the proximal end of the lip toward the distal end of the lip.

In an embodiment, the device further includes a proximally projecting handle, the handle extending proximally beyond the proximal end of the housing; and an array of illuminating elements distributed around a circumference of the housing to enhance visualization of tissue.

In an embodiment, the device is illuminating elements are LEDs. The LEDs also include a secondary Narrow Band Imagining capability.

The present disclosure also relates to a method for ligating tissue which includes inserting a device into an anal cavity, the device including an elongated hollow transparent housing with an open proximal end, a lip attached to the proximal end of the housing, a lumen extending though the interior of the housing to a distal tip, and a first port extending through a lateral wall of the housing; rotating the housing until a first target portion of tissue is exposed to the lumen via the first port; and drawing the first target portion of tissue through the first port.

In an embodiment, a treatment device is inserted into the lumen to treat the first target portion of tissue. The device includes a first ligation band extending around the first port, a second port and a second ligation band extending around the second port.

In an embodiment, a first trigger line extends proximally from the first ligation band, the method further comprising drawing the first trigger line proximally out of the lumen so that the first trigger line pulls the first ligation band off of the device.

In an embodiment, the housing includes a first lever member on the lateral wall of the housing abutting the first ligation band and a second lever member on the lateral wall of the housing abutting the second ligation band, the method further comprising pushing the first lever member radially outward so that the first lever member pushes a first tab radially outward to push the first ligation band off of the device and, after the first ligation band has been pushed off of the device, repositioning the device to receive a second target portion of tissue through the second port and pushing the second lever member radially outward so that the second lever member pushes a second tab radially outward to push the second ligation band off of the device.

In an embodiment, the method further includes activating an array of illuminating elements to illuminate the anal cavity.

In an embodiment, the method further includes drawing a vacuum to pull the first target portion of tissue through the first port into the lumen by drawing a plunger proximally through the housing to apply a vacuum pressure to the first port to draw the first target portion of tissue into the lumen; and releasing the first ligation band from the first port to constrict around the first target portion of tissue.

In an embodiment, the vacuum is produced by connecting the lumen of the housing to an external source of negative fluid pressure, the method further comprising releasing the first ligation band from the first port to constrict around the first target portion of tissue.

BRIEF DESCRIPTION

FIG. 2 shows a perspective view of a device for inspecting and treating hemorrhoids according to a second embodiment;

FIG. 6 shows a close-up side view of the band deployment mechanism of the device of FIG. 4 with no ligation band received thereon;

FIG. 7 shows a perspective view of a device for inspecting and/or treating hemorrhoids according to a fourth embodiment;

FIG. 11 shows an end view of the device of FIG. 10; and

DETAILED DESCRIPTION

Figure 1:
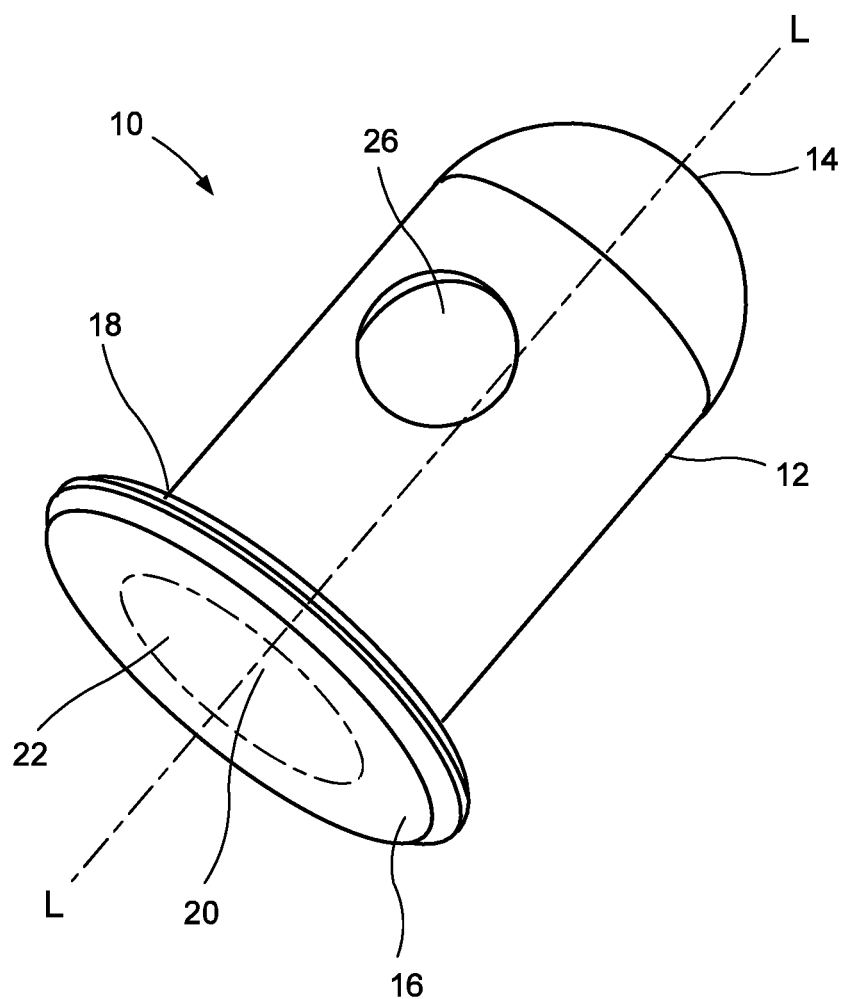
FIG. 1 shows a perspective view of a device for inspecting and treating hemorrhoids according to a first exemplary embodiment of the present disclosure.

The present disclosure may be further understood with reference to the following description and the appended drawings, wherein like elements are referred to with the same reference numerals. The present disclosure is directed to a device for inspecting and/or treating internal hemorrhoids. It is noted that the terms proximal and distal, as used herein, refer to a direction toward (proximal) and away from (distal) a user of the device.

As shown in FIG. 1, a device 10 for inspecting and/or treating internal hemorrhoids includes a housing 12 sized and shaped for insertion into the anus. The housing 12, in this embodiment, is substantially cylindrical with a blunted distal end 14 to minimize trauma during insertion. However, those skilled in the art will understand that the dimensions of the housing 12 may be altered to suit the anatomy of the patient and/or the location (i.e., depth within the body) of the hemorrhoids to be inspected and/or treated. The device 10 includes a radially protruding lip 16 at the proximal end 18 of the housing 12 and forms a lumen 20 extending within the device from a proximal opening 22 to the distal end 14 of the housing 12. The housing 12 is transparent so that a user may view the anatomy surrounding the housing 12 from the proximal end (i.e., via the lumen 20). However, some elements such as the band deployment mechanism, various small parts such as the ligation bands, or the lip, may be opaque or less than fully transparent.

The housing 12 in this embodiment may be formed of any suitable biocompatible transparent material such as an optically clear plastic (e.g., injection molded polycarbonate, acrylic thermoplastics, etc.). The housing 12 includes a surgical port 26 formed as an opening in the cylindrical side surface of the housing 12 and which extends through the wall of the housing to open to the lumen 20. The size and shape of the surgical port 26, in this embodiment, are selected to permit a hemorrhoid to be received therein. That is, a diameter of the surgical port 26 is selected so that, when drawn into the lumen 20 via the surgical port 26, the base of the hemorrhoid and a small portion of non-hemorrhoidal surrounding tissue may also be drawn through the port 26 into the lumen 20.

In use, for example, the distal end 14 of the device 10 may be inserted into the anus of a patient and advanced into the anus under visual control by a user observing the tissue surrounding the housing 12 via the proximal opening 22 of the lumen 20 as the tissue will be visible through the transparent surface of the housing 12 while the user will be able to view tissue distal of the distal end 14 of the housing 12 via the transparent distal end 14. Thus, the user may advance the housing 12 into the body until the target tissue (e.g., a hemorrhoid to be inspected and/or treated) is aligned along a proximal to distal axis L with the port 26. The user may then manually rotate the housing 12 via the lip 16 at the proximal end of the device until the target tissue (i.e., the hemorrhoid) is exposed to the lumen 20 via the port 26. At this point, the hemorrhoid may protrude into the lumen 20 on its own. The user may then introduce treatment devices such as graspers, clips, snares, etc. into the device 10 via the proximal opening 22 and inspect and/or treat the hemorrhoid as desired. For example, a user may use a grasper (not shown) to draw the hemorrhoid further into the lumen 20 to visually inspect the hemorrhoid and, if desired, introduce a treatment device into the lumen 20 to treat the hemorrhoid.

Alternatively, suction may be applied to the proximal end of the device 10 to draw tissue into the lumen 20. A user may then, for example, excise the tissue, place a ligation band around the target tissue, cauterize the tissue, etc. using any of a large variety of known devices. The user may then visually inspect the target tissue or treatment site through the device 10 and, when the tissue has been treated as desired, may remove the device 10 from the body or reposition the device 10 in the same manner described above to inspect and/or treat a second portion of tissue.

As shown in FIG. 2, a device 110 according to a second embodiment is similar to the device 10 except that the device 110 also includes a ligation band 132 mounted around the surgical port 126 along with a mechanism for deploying the ligation band 132. In some embodiments, the device 110 for inspecting and/or treating internal hemorrhoids includes a housing 112 (e.g., cylindrical) sized and shaped for insertion into the anus with a blunted distal end 114 to minimize trauma during insertion.

The device 110 includes a radially protruding lip 116 at the proximal end 118 of the housing 112 and forms a lumen 120 extending within the device from a proximal opening 122 to the distal end 114 of the housing 112. As with the device 10, the housing 112 is transparent so that a user may view the anatomy surrounding the housing 112 from the proximal end (i.e., via the lumen 120). The housing 112 includes a surgical port 126 formed as an opening in the cylindrical side surface of the housing 112 and which extends through the wall of the housing 112 to open to the lumen 120.

Similarly to the device 10, the size and shape of the surgical port 126, in this embodiment, are selected to permit a hemorrhoid to be received therein. The surgical port 126 of this embodiment is formed on a generally flat surface 128 recessed into the surface of the wall of the housing 112 and includes a lip 130 protruding outward from the surface 128 by a distance selected to exceed the thickness of the ligation band 132 to be received therearound. In this embodiment, the lip 130 extends around an entire circumference of the port 126. However, those skilled in the art will understand that the lip 130 may extend around only a portion of the circumference of the port 126 or may be formed as separate members spaced around the circumference to stretch the ligation band 132 around the port 126 as desired.

Figure 3:
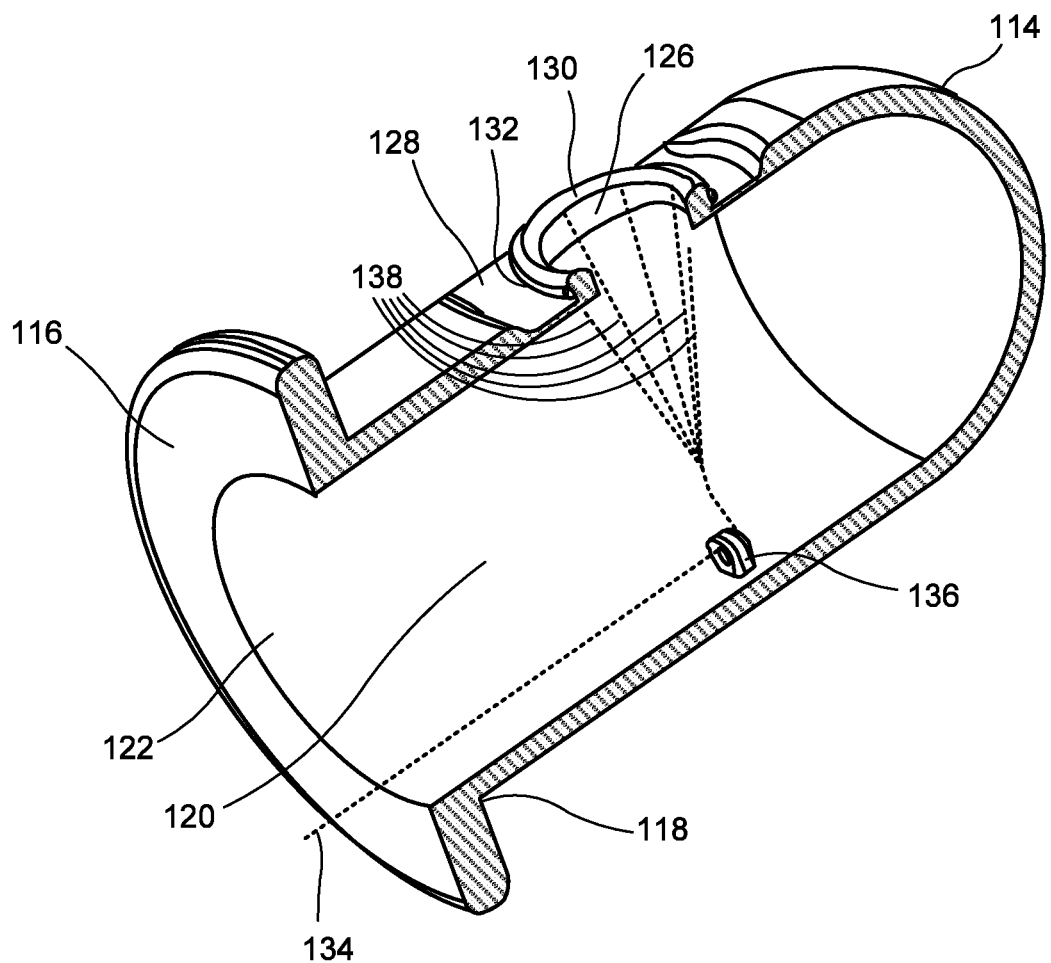
FIG. 3 shows a partially cutaway view of the device of FIG. 2.

As would also be understood by those skilled in the art, the ligation band 132 is stretched around the lip 130 so that, when released from the lip 130, the ligation band 132 contracts around any tissue received through the port 126. In addition, the surface 128 is recessed relative to surrounding portions of the wall of the housing 112 by a distance selected so that the lip 130 does not extend radially outward from the longitudinal axis L of the device 110 beyond the surrounding portions of the housing 112 (i.e., in this embodiment, the lip 130 does not expand the outer profile of the device 110. A trigger line 134 extends into the lumen 120 via the opening 122 and passes into the lumen 120 to a redirecting eye 136 located, in this embodiment, diametrically opposed to the port 126 so that the trigger line 134 passes across the lumen 120 generally transverse to the axis L, exits the port 126 and is wrapped under and around the ligation band 132 in a known manner so that, when a user draws the trigger line 134 proximally out of the opening 122, the trigger line 134 pulls the ligation band 132 radially outward off of the lip 130 so that the ligation band 132 contracts around any tissue that has been drawn through the port 126 into the lumen 120. For example, the trigger line 134 may be a tether, filament, suture, wire, or other connector disposed to actuate the ligation band in response to a medical professional pulling the trigger line 134 in a proximal direction In this embodiment, as can be seen in FIG. 3, a portion of the trigger line extending between an eye 136 and the port 126 is split into a plurality of filaments 138 (in this embodiment there are 8 filaments 138) that are spread circumferentially about the lip 130 so that tension applied to the proximal end of the trigger line 134 is spread out about the circumference of the ligation band 132 to facilitate a more even release of the ligation band 132 from the lip 130. However, as would be understood any desired number of filaments 138 may be employed as desired. In some embodiments, a single strand trigger line 134 may extend from the proximal end through the eye 136 to the ligation band 132 if desired.

In use, for example, the distal end 114 of the device 110 is inserted into the anus of a patient and advanced into the anus under visual control by a user observing the tissue surrounding the housing 112 via the proximal opening 122 of the lumen 120 as the tissue will be visible through the transparent surface of the housing 112 while the user views tissue distal of the distal end 114 of the housing 112 via the transparent distal end 114. The user advances the housing 112 into the body until the target tissue (e.g., a hemorrhoid to be inspected and/or treated) is aligned along a proximal to distal axis L with the port 126. The user then manually rotates the housing 112 via the lip 116 at the proximal end of the device 110 until the target tissue (i.e., the hemorrhoid) is exposed to the lumen 120 via the port 126. At this point, the hemorrhoid may protrude into the lumen 120 on its own.

The user may then introduce treatment devices such as graspers, clips snares, etc. into the device 110 via the proximal opening 122 and inspect and/or treat the hemorrhoid as desired. For example, a user may use a grasper to draw the hemorrhoid further into the lumen 120 to visually inspect the hemorrhoid and, if desired, may, when the hemorrhoid has been drawn into the lumen 120 to a desired extent, deploy the ligation band 132 from the lip 130 so that the ligation band constricts around the target tissue at the point where the tissue is adjacent to the lip 130. The user may then introduce any further treatment device(s) into the lumen 120 to treat the hemorrhoid as described above.

The user may then reposition the device to inspect and/or treat a second target portion of tissue (e.g., a second hemorrhoid) in the same manner described above. However, as the device 110 according to this embodiment has only a single ligation band 132, if a user wants to treat a second hemorrhoid, without removing the device 110 from the body, the user must use a separate tissue treatment device (as described above in regard to the device 10). A user may, alternatively, remove the device 110 from the body and reload it with another ligation band 132 and couple the new band 132 to the trigger line 134 in the same manner as the trigger line 134 was coupled to the first ligation band 132. The device 110 may then be reinserted to ligate a second hemorrhoid in the same manner described above.

Figure 4:
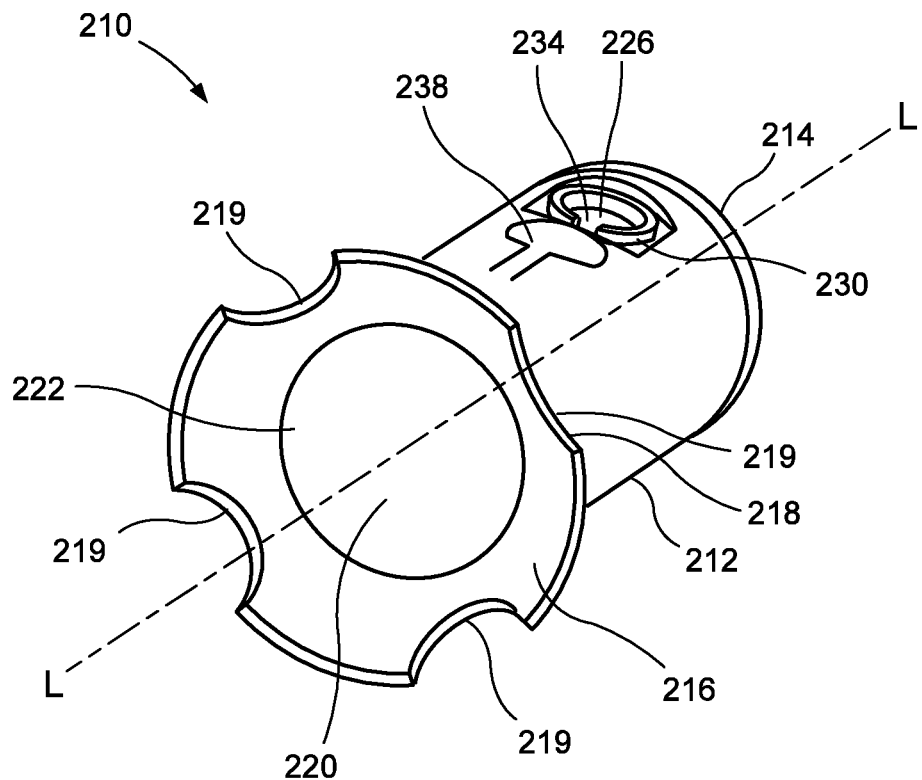
FIG. 4 shows a perspective view of a device for inspecting and/or treating hemorrhoids according to a third embodiment.
Figure 5:
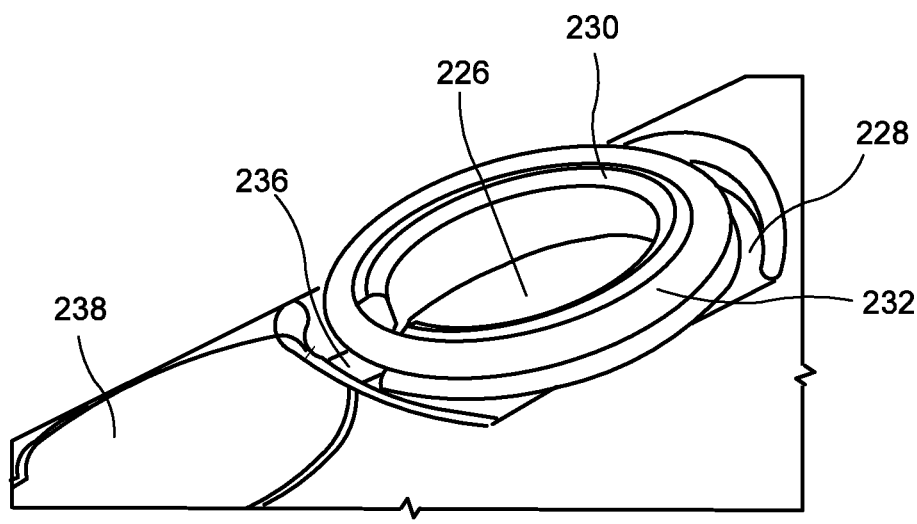
FIG. 5 shows a close-up view of a band deployment mechanism of the device of FIG. 4 with a ligation band received thereon.

As shown in FIGS. 4-6, a device 210 according to a third embodiment is similar to the device 110 except that the device 210 includes a different mechanism for deploying a ligation band 232 mounted around its surgical port 226 and includes a differently structured lip 216 at its proximal end. In some embodiments, the device 210 for inspecting and/or treating internal hemorrhoids includes a transparent housing 212 sized and shaped for insertion into the anus with a blunted distal end 214 to minimize trauma during insertion. The radially protruding lip 216 at the proximal end 218 of the housing 212 bends proximally away from the point at which it is attached to the proximal end 218 of the housing 212. In this embodiment, the lip 216 extends along a surface that forms a portion of a sphere abutting the proximal end 218 of the housing 212. However, those skilled in the art will understand that the specific shape of this lip 216 may be changed without departing from the scope of the embodiment.

In addition, the lip 216 of this embodiment includes a plurality of (in this case four) finger grips 219 formed as indentations projecting radially into the lip 216. It is noted any of the embodiments herein may also include finger grips as described here. The finger grips 219 facilitate the rotation of the housing 212 within the anus by increasing a user's ability to grip the lip 216 and apply torque thereto. The housing 212 forms a lumen 220 therein. As with the device 10, the housing 212 is transparent so that a user may view the anatomy surrounding the housing 212 from the proximal end (i.e., via the lumen 220). The surgical port 226 of the device 210 is also formed as an opening in the side surface of the housing 212 which extends through the wall of the housing 212 to open to the lumen 220.

Similarly to the device 110, the size and shape of the surgical port 226, in this embodiment, are selected to permit a hemorrhoid to be received therein. The surgical port 226 of this embodiment is formed on a generally flat surface 228 recessed into the surface of the wall of the housing 212 and includes a lip 230 protruding outward from the surface 228 by a distance selected to exceed the thickness of the ligation band 232 stretched therearound. However, those skilled in the art will understand that the ligation band 232 may project outward from the housing 212 by a small distance.

In this embodiment, the lip 230 does not extend around an entire circumference of the port 226. Rather, a gap 234 is formed in the lip 230 of this embodiment at a location corresponding to a tab 236 which resides radially underneath the ligation band 232 so that, as the tab 236 is deflected radially outward away from the axis L, the tab 236 pushes the ligation band 232 radially outward off of the lip 230 so that the ligation band 232 is deployed from the lip 230 and constricts around any tissue that has been drawn into the lumen 220 via the port 226. In some embodiments, the tab is connected to a lever member 238 which has been partially separated from surrounding parts of the housing 212 so that, if a user presses their finger radially outward against the inner surface of the lever member 238 (i.e., the surface of the lever member 238 forming the surface of the lumen 220), the lever member 238 and the tab 236 are deflected radially outward away from the axis L to deploy the ligation band 232. The lever member 238 and the tab 236 then return to the neutral position when the user releases the force from the tabs.

In use, for example, the distal end 214 of the device 210 is inserted into the anus of a patient and advanced as the user observes tissue surrounding the housing 212 via the proximal opening 222 of the lumen 220 through the transparent surface of the housing 212. The user advances the housing 212 into the body until the target tissue (e.g., a hemorrhoid to be inspected and/or treated) is aligned along a proximal to distal axis L with the port 226. As described above, the user grasps the lip 216 via the finger grips 219 and manually rotates the housing 212 until the target tissue (i.e., the hemorrhoid) is exposed to the lumen 220 via the port 226. The user then draws the target tissue into the lumen 220 using, for example, graspers, suction, and the like as would be understood by those skilled in the art.

When the hemorrhoid has been drawn into the lumen 220 to a desired extent, the user may deploy the ligation band 232 from the lip 230 so that the ligation band constricts around the target tissue at the point where the tissue is adjacent to the lip 230. In some embodiments, when the hemorrhoid (or other target tissue) has been drawn into the lumen 220 via the port 226 as desired, the user reaches in with a finger or other instrument and applies pressure radially outward against the inner surface of the lever member 238 to deflect the tab 236 outward. This pushes the ligation band 232 off of the lip 230 so that the ligation band 232 constricts about the tissue that has been drawn into the port 226.

The device 210 according to this embodiment has only a single ligation band 232 mounted thereon. Thus, if a user wants to treat a second hemorrhoid, without removing the device 210 from the body, the user must use a separate tissue treatment device (as described above in regard to the device 110). A user may, alternatively, remove the device 210 from the body and reload it with another ligation band 232. The device 210 may then be reinserted to ligate a second hemorrhoid in the same manner described above.

Alternatively, the lip 230 may be sized to hold multiple ligation bands 232 so that more than one hemorrhoid may be ligated without removing the device 210 from the body to load on additional ligation bands 232. In some embodiments, the ligation bands 232 may be placed around the lip 230 with a first ligation band 232 closest to the tab 236 and successive bands 232 in series moving away from the tab 236 to a final ligation band 232 that is closest to a free end of the lip 230 furthest from the tab 236. Thus, each time the user deflects the lever member 238 and the tab 236 radially outward, the final ligation band 232 is deployed from the lip 230 while each subsequent ligation band 232 moves closer to the free end of the lip 230. Thus, each actuation of the lever member 238 will dispense a further ligation band 232 until all of the bands 232 have been deployed.

FIG. 7 shows a device 310 according to a fourth embodiment that is similar to the device 210 except that the device 310 includes multiple ports 326 that are distributed circumferentially around the cylindrical side wall of the transparent housing 312. Each of the ports 326 of this embodiment includes a ligation band deployment mechanism substantially identical to that described above in regard to the device 210. That is, each of the ports 326 of the device 310 includes a corresponding tab 336 extending from a lever member 338 so that, when a lever member 338 is deflected radially outward as described above, the corresponding tab 336 is moved outward deploying a ligation band 332 from the corresponding port 326.

When a user wants to ligate multiple hemorrhoids, the user operates the device 310 in the same manner as described above in regard to device 210 for the first hemorrhoid and, when the first hemorrhoid has been successfully ligated, the user re-positions the device 310 so that a second hemorrhoid is received within a second one of the ports 326. The user then operates the device 310 in the same manner described above for the device 210 and continues in this manner until all the target hemorrhoids have been ligated or until each of the ligation bands 332 has been deployed from its corresponding lip 330. It is noted that, in this embodiment, all of the ports 326 are substantially aligned longitudinally along the device 310. That is, each of the ports 326 is positioned at a location (distal to proximal) that is substantially the same as the other ports 326.

As would be understood by those skilled in the art, the ports 326 may be located in any position or arrangement longitudinally or circumferentially as desired. For example, the ports 326 may be staggered with respect to one another longitudinally so that a first one of the ports 326 may be positioned to more easily treat hemorrhoids that are located more deeply within the rectum while others of the ports 326 may be positioned to facilitate treatment and/or inspection of hemorrhoids located closer to the anus. Moreover, a desirable configuration of the ports 326 would be to have two ports 326 located more distally on the device 310 and two ports 326 located more proximally on the device 310.

Figure 8:
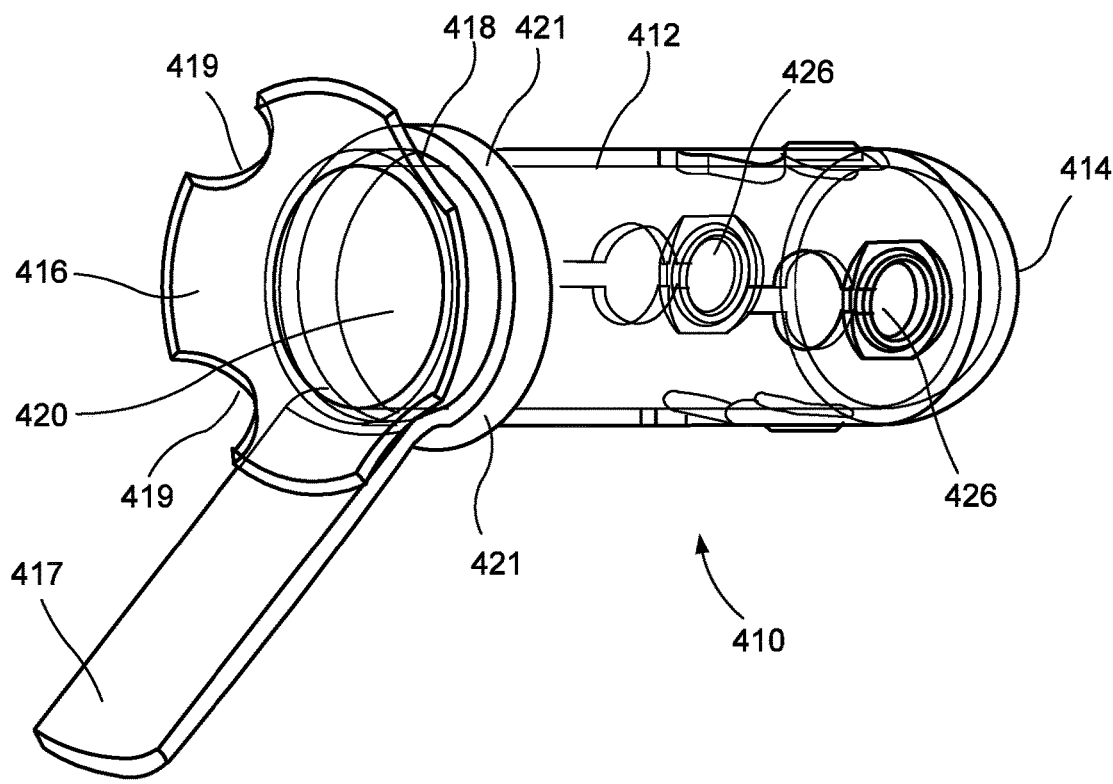
FIG. 8 shows a perspective view of a device for inspecting and/or treating hemorrhoids according to a fifth embodiment.

A device 410 as shown in FIG. 8 is substantially similar to the device 310 except that the device 410 includes a proximally projecting handle 417 and an array of illumination elements 421 aimed to project illumination distally toward the target tissue to enhance a user's ability to observe the tissue adjacent to the device 410. In some embodiments, the device 410 according to a fifth embodiment includes a transparent housing 412 extending from a proximal end 418 to a distal end 414 and forming a lumen 420 therebetween. Similarly to the device 310, the device 410 includes a lip 416 at a proximal end thereof including finger grips 419.

In addition, the device 410 includes a handle 417 that projects proximally over the distal surface of the lip 416 and extends proximally beyond the proximal end of the lip 416 to remain easily accessible to the user to facilitate the positioning and manipulation of the device 410 when the housing 412 is inserted into the body. In addition, the device 410 includes an array of illumination elements (e.g., LEDs) that provide illumination of one or more frequencies of light to enhance visualization of target tissue. In some embodiments, the LEDs of this embodiment are distributed around the circumference of the housing 412 facing distally to direct illumination toward the ports 426 and toward the distal end 414 of the device 410 generally to aid in the visualization of tissues adjacent to the device 410. The LEDs may emit white light or may also include a secondary Narrow Band Imaging (NBI) capability for detailed imaging of vascular/mucosal tissue.

In use, the device 410 is operated in substantially the same manner as described in regard to the device 310 except that here, a user may engage the illumination elements 421 at any time and in any desired pattern to aid in visualizing tissue and may use the handle 417 with or separately from the lip 416 to position and rotate the device as desired.

Figure 9:
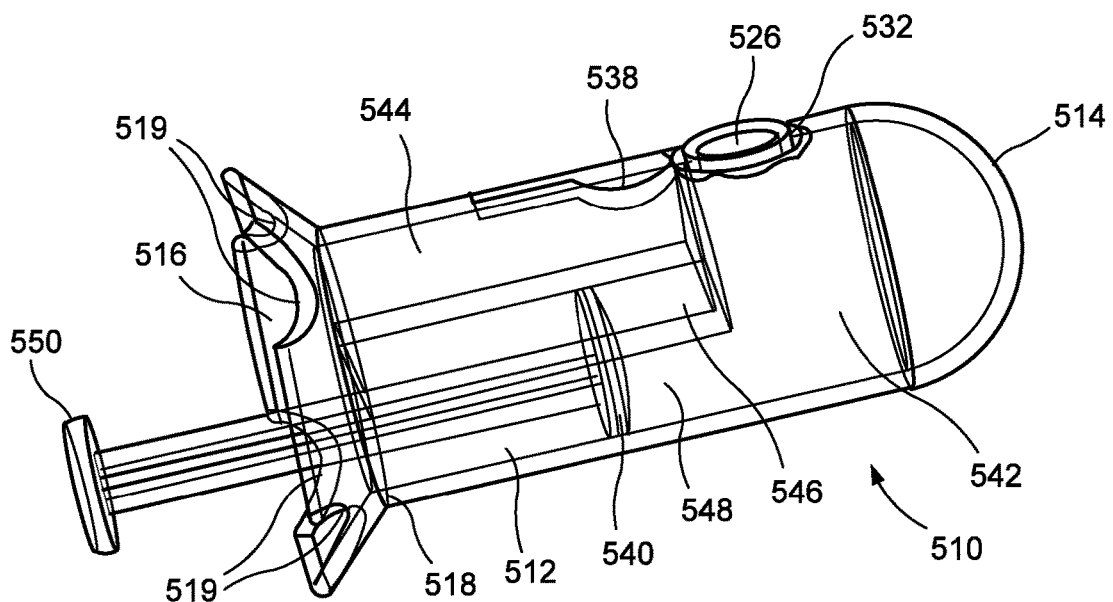
FIG. 9 shows a perspective view of a device for inspecting and/or treating hemorrhoids according to a sixth embodiment.

FIG. 9 shows a device 510 according to a sixth embodiment. The device 510 is in many respects similar to the device 210 including a substantially similar mechanism for deploying a ligation band 532 except that the device 510 includes a plunger 540 and a vacuum chamber 542 permitting a user to apply vacuum pressure to the port 526 to draw target tissue into the vacuum chamber 542 through the port 526. Those skilled in the art will understand that this arrangement may assist in the inspection and/or treatment of low-grade hemorrhoids which have not prolapsed or do not otherwise protrude significantly from surrounding tissue. That is, the suction applied may help in these embodiments to draw an increased amount of tissue through the port 526 so that the hemorrhoid may be more completely ligated than with other methods of drawing such non-prolapsed tissue through the port 526. In some embodiments, the device includes a transparent housing 512 extending from a proximal end 518 to a distal end 514. Similarly to the device 210, the device 510 includes a lip 516 at a proximal end thereof including finger grips 519.

In contrast to the device 210, the interior of the housing 512 is divided into a vacuum chamber 542 and a ligation band deploying chamber 544 via which a user can actuate a lever member 538 as described above to deploy a ligation band 532. In some embodiments, an interior of the housing 512 is separated by a wall 546 into the ligation band deploying chamber 544 and the vacuum chamber 542 with the wall 546 preventing the flow of air between these chambers. The vacuum chamber 542 extends from the proximal end 518 into the housing 512 beyond a distal end of the ligation band deploying chamber 544 so that the port 526 opens into the vacuum chamber 542.

The plunger 540 is received within a proximal portion 548 of the vacuum chamber 542 with a shape of the plunger closely matching a shape of the interior of the proximal portion 548 so that, as the plunger 540 is moved proximally through the proximal portion 548, a vacuum is drawn in the vacuum chamber applying negative fluid pressure to the exterior of the housing 512 via the port 526. Moving the plunger distally through the proximal portion 548 forces air out of the vacuum chamber 542 via the port 526. The plunger 540 is coupled to a handle 550 that projects proximally out of the device 510 so that a user may move the plunger 540 within the vacuum chamber as desired while the device 510 is inserted into the body.

In use, the device 510 is positioned as described above so that the port 526 opens to the target tissue. The user has preferably positioned the device 510 in this manner while maintaining the plunger 540 in its distal-most position so that, when the device 510 is positioned as desired, the user may pull the handle 550 proximally out of the housing 512 to draw the plunger 540 proximally through the proximal portion 548. This, in turn, draws a vacuum in the vacuum chamber 542 applying suction to the port 526 and drawing the hemorrhoid into the vacuum chamber via the port 526. The user then reaches into the ligation band deploying chamber 544 to push the lever member 538 outward deploying the ligation band 532 around the tissue that has been drawn through the port 526 into the vacuum chamber 542.

Figure 10:
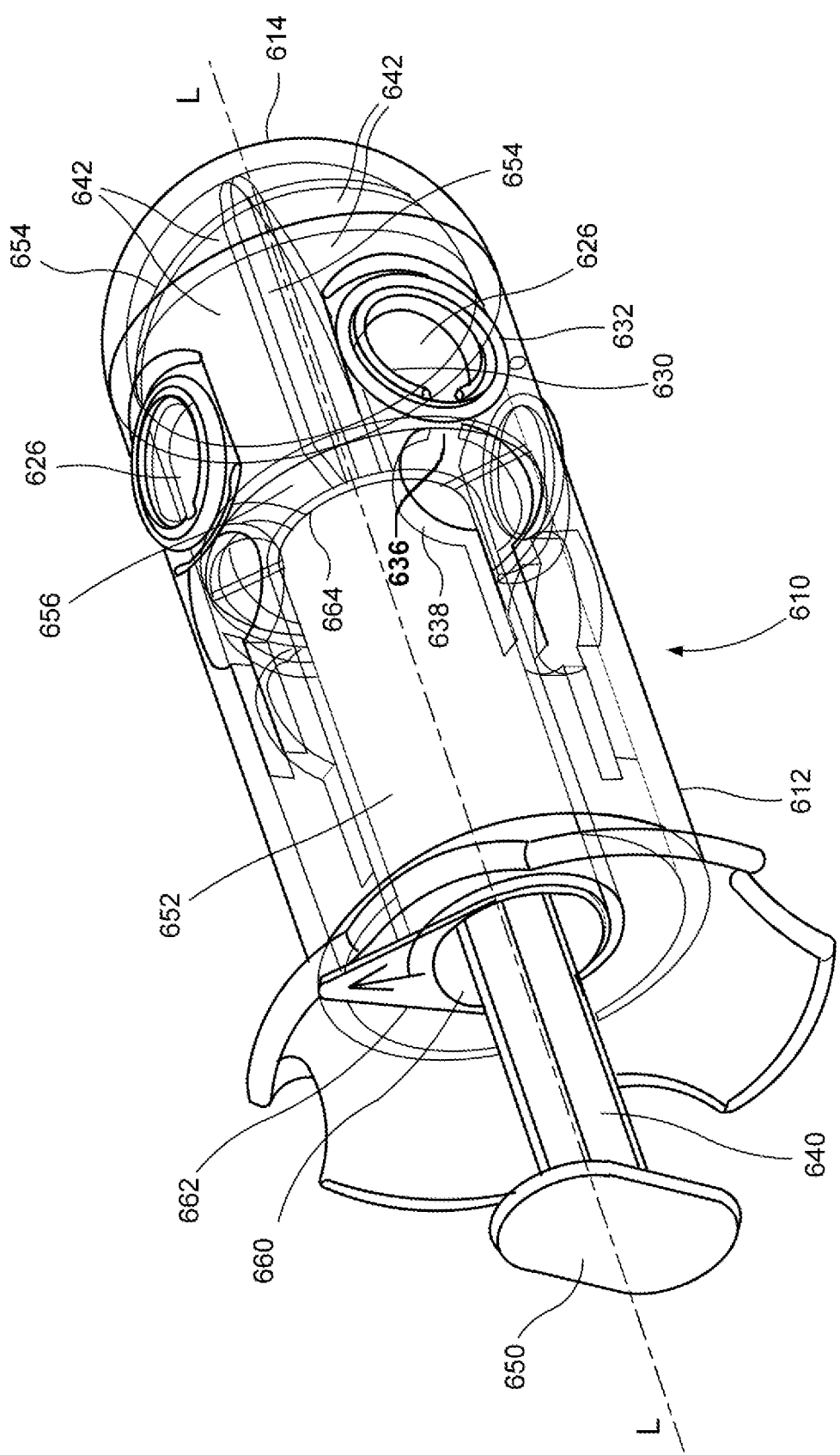
FIG. 10 shows a perspective view of a device for inspecting and/or treating hemorrhoids according to a seventh embodiment.

FIGS. 10 and 11 show a device 610 according to a seventh embodiment that is similar in many respects to the device 510 except that this device includes multiple ports 626 each of which may be isolated from the others so that suction drawn by a plunger 640 via a handle 650 is applied only to a selected one of the ports 626. In some embodiments, in the device 610, the plunger 640 is slidably and snugly received in a plunger chamber 652 so that drawing the plunger 640 proximally through the plunger chamber 652 draws a vacuum in the portion of the chamber extending distally from the plunger 640. A distal portion of housing 612 (e.g., toward distal end 614) into which each of the ports 626 opens is divided into four separate vacuum chambers 642, each sealed from the others with each port 626 opening into a corresponding one of the chambers 642.

The vacuum chambers 642 are separated from one another by two longitudinally extending walls 654 and a transverse wall 656 that extends across the housing 612 transverse to the longitudinal axis L and which completely seals the four vacuum chambers 642 from the portions of the interior of the housing 612 proximal of the transverse wall 656. Four holes 658 extend through the transverse wall 656 within the perimeter of the plunger chamber 652 with each of the holes 658 opening into a corresponding one of the vacuum chambers 642. The device 610 further includes a vacuum selector member 660 that extends within the plunger chamber 652 from a proximal indicator 662 to a distal sealing member 664. The distal sealing member 664 is pressed against, extends over and seals the holes 658. The distal sealing member 664 includes a single hole 666 which, depending on the orientation of the vacuum selector member 660, aligns with a single one of the holes 658 to permit fluid flow between the plunger chamber 652 and a selected one of the vacuum chambers 642.

In some embodiments, the vacuum selector member 660 is rotatably received within the plunger chamber 652 so that a user may rotate the vacuum selector member 660 until the proximal indicator 662 points to a selected one of the ports 626 into which it is desired to draw a target hemorrhoid. At this point, the holes 666 in the distal sealing member will be open to the hole 658 in the transverse wall 656 of the vacuum chamber 642 corresponding to the selected port 626. Thus, the plunger chamber 652 is fluidly coupled to the selected port 626 so that, drawing the plunger 640 proximally through the plunger chamber 652 draws the target hemorrhoid into the corresponding vacuum chamber 642 via the selected port 626.

The user may then deploy the ligation band 632 from the selected port 626 by reaching into a ligation band deploying chamber 644 that extends annularly around the plunger chamber 652 and moving a lever member 638 corresponding to the selected port 626 outward to deflect a tab 636 outwards to push the ligation band 632 off of a lip 630 allowing the ligation band 632 to constrict around the tissue that has been drawn into the corresponding vacuum chamber 642 via the selected port 626. The user may then reposition the device 610 as desired and repeat this process using the other ports 626 to ligate additional hemorrhoids.

Figure 12:
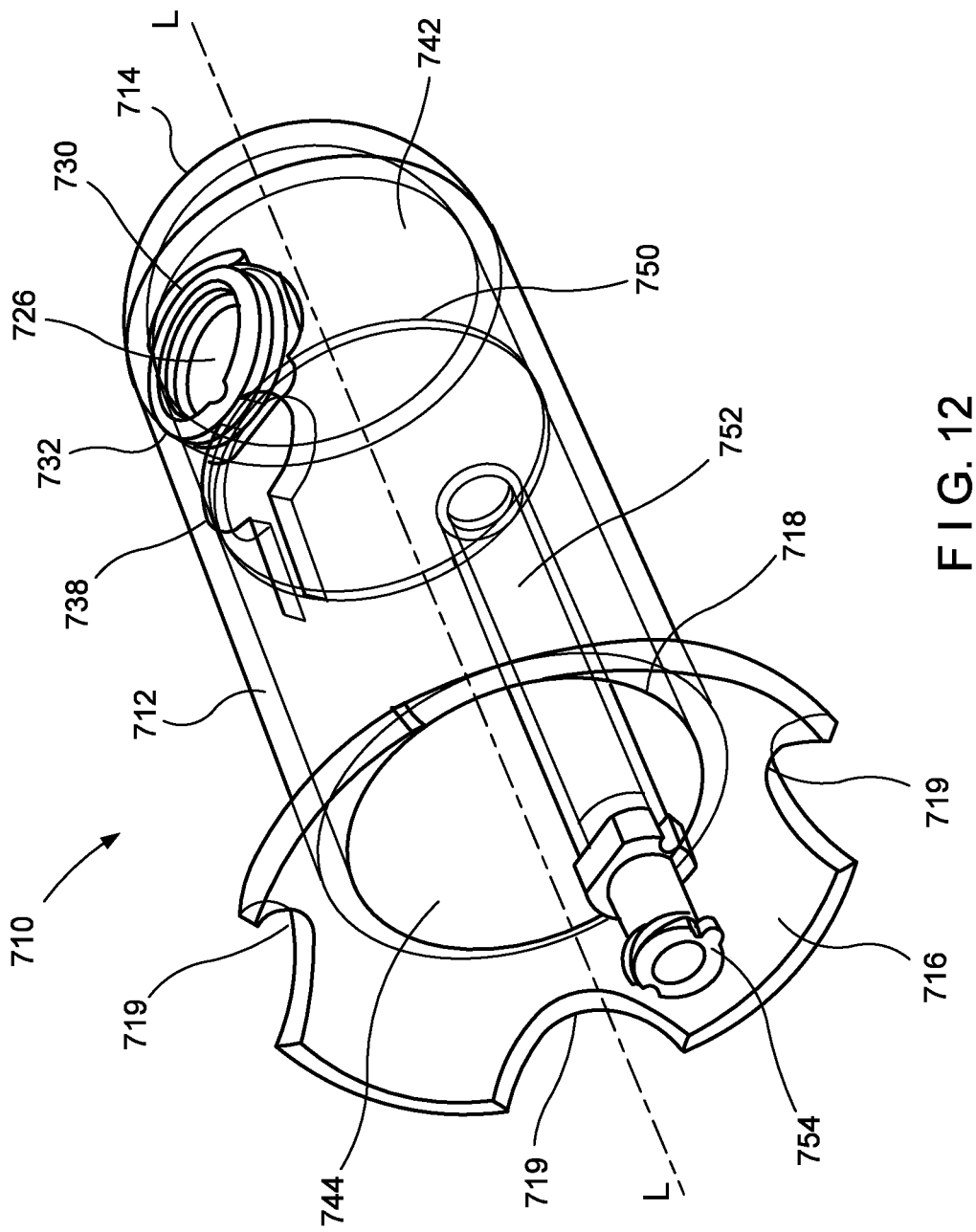
FIG. 12 shows a perspective view of a device for inspecting and/or treating hemorrhoids according to an eighth embodiment.

FIG. 12 shows a device 710 according to an eighth embodiment. The device 710 is in many respects similar to the device 510 including a substantially similar mechanism for deploying a ligation band 732 from a lip 730 except that, to draw suction through the port 726, the device 710 includes a lumen for connection to an external source of negative fluid pressure. Similarly to the devices 510 and 610, the device 710 may assist in the inspection and/or treatment of low grade hemorrhoids which have not prolapsed or do not otherwise protrude significantly from surrounding tissue. That is, the suction applied may help in these embodiments to draw an increased amount of tissue through the port 726 so that the hemorrhoid may be more completely ligated than might be the case with other methods of drawing such non-prolapsed tissue through the port 726.

In some embodiments, the device 710 includes a transparent housing 712 extending from a proximal end 718 to a distal end 714. The device 710 includes a lip 716 at a proximal end thereof including finger grips 719 substantially similarly to the device 510. In contrast to the device 510, the interior of the housing 712 is divided into a vacuum chamber 742 and a ligation band deploying chamber 744 via which a user can actuate the lever member 738 as described above to deploy a ligation band 732. In some embodiments, the interior of the housing 712 is separated by a wall 750 extending transverse to the longitudinal axis L of the device 710 into the ligation band deploying chamber 744 and the vacuum chamber 742 with the wall 750 preventing the flow of air between these chambers.

The vacuum chamber 742 extends distally from the wall 750 to the distal end 714 of the housing 712 with the port 726 opening into the vacuum chamber 742. The portion of the interior of the housing extending proximally from the wall 750 is designated the ligation band deploying chamber 744 as it provides space for the user to reach in and actuate the lever member 738 to deploy a ligation band 732 in the same manner described above. A tube 752 extending proximally from the wall 750 includes a lumen open to the vacuum chamber 742. The tube 752 extends to a coupling 754 (in this embodiment a luer lock) configured to couple the tube 752 to a source of negative fluid pressure so that this negative pressure may be applied through the tube 752 and the vacuum chamber 742 to the port 726. The operation of the device 710 is substantially the same as that of the device 510 except that, in this case, when the user desires to apply negative pressure to suck target tissue into the vacuum chamber 742 via the port 726, the user simply connects the supply of negative pressure to the tube 752 via the coupling 754. For example, the source of negative fluid pressure may be a vacuum pump, a syringe, etc.

Those skilled in the art will understand that there are various modifications that may be made to the embodiments described without departing from the teachings of this application. For example, although the embodiments have been described in regard to the treatment of internal hemorrhoids, those skilled in the art will understand that the described embodiments may also be implemented for other treatments, e.g., polyps. In addition, as would be understood by those skilled in the art any of the features of any one of these embodiments may be combined with any of the features of any of the other embodiments so long as the elements are not inconsistent with one another. For example, in an embodiment with multiple ports each of which includes a ligation band, a first one of the ligation bands may be deployed via a trigger line deployment mechanism as described while another is deployed via the lever and tab mechanism, etc.

The invention claimed is:

1. A device, comprising:
an elongated housing formed of an optically transparent material, the housing extending from a proximal end to a distal end and including a lateral wall extending from the proximal end to a distal tip of the housing, the housing defining a lumen extending into the housing from a proximal opening in the proximal end of the housing;
a first port extending through the lateral wall of the housing to open the lumen of the housing to an exterior of the housing, the first port being sized and shaped to receive therein a target portion of tissue to be inspected and/or treated;
a first ligation band holding structure surrounding the first port, the first ligation band holding structure configured to stretch a first ligation band around the first port so that, tissue drawn into the lumen of the housing via the first port passes through the first ligation band; and
a first ligation band deploying mechanism selectively operable to deploy the first ligation band from the first ligation band holding structure so that the first ligation band constricts around any tissue extending through the first port, the first ligation band deploying mechanism including a tab formed as a part of the housing movable relative to adjacent portions of the housing, the tab being located adjacent to the first port so that, the tab abuts a portion of a ligation band received around the first port, movement of the tab relative to the adjacent portions of the housing moving the ligation band out of engagement with the first ligation band holding structure.

2. The device of claim 1, wherein the housing is sized and shaped for insertion into a rectum and the first port is sized and shaped to receive a hemorrhoid therein so that a user may view the hemorrhoid and tissue adjacent to the housing through a transparent housing via the proximal opening of the lumen of the housing.

3. The device of claim 1, further comprising:
a second port extending through the lateral wall of the housing to open the lumen of the housing to an exterior of the housing, the second port being sized and shaped to receive therein a target portion of tissue to be inspected and/or treated;
a second ligation band holding structure surrounding the second port, the second ligation band holding structure configured to stretch a second ligation band around the second port so that, tissue drawn into the lumen of the housing via the second port passes through the second ligation band; and
a second ligation band deploying mechanism selectively operable to deploy the second ligation band from the second ligation band holding structure so that the second ligation band constricts around any tissue extending through the second port.

4. The device of claim 3, further comprising:
a first vacuum chamber formed within the housing and in fluid communication with the first port;
a second vacuum chamber formed within the housing and in fluid communication with the second port; and
a source of negative fluid pressure selectively couplable to a selected one of the first and second vacuum chambers to apply suction to the corresponding one of the first and second ports to draw target tissue into the corresponding one of the first and second vacuum chambers.

5. The device of claim 4, further comprising:
a port selection mechanism that couples the source of negative pressure to the selected one of the first and second vacuum chambers, the port selection mechanism including a sealing member that abuts a wall that seals the first and second vacuum chambers, the wall including a first hole opening a plunger chamber to the first port and a second hole opening the plunger chamber to the second vacuum chamber, the sealing member being movable between a first configuration in which the first hole opening is open and the second hole opening is sealed and a second configuration in which the second hole opening is open and the first hole opening is sealed,
wherein the source of negative fluid pressure includes a plunger slidably mounted within the first vacuum chamber so that, drawing the plunger proximally through the first vacuum chamber draws negative pressure in the first vacuum chamber to apply suction to the first port.

6. The device of claim 5, wherein the source of negative fluid pressure includes a plunger slidably mounted within the lumen of the housing so that, drawing the plunger proximally through the lumen of the housing draws negative pressure in the selected one of the first and second vacuum chambers to apply suction to the one of the first and second ports that corresponds to the selected one of the first and second vacuum chambers and wherein the sealing member is rotatably received within the lumen of the housing.

7. The device of claim 1, further comprising:
a first vacuum chamber formed within the housing and in fluid communication with the first port; and
a source of negative fluid pressure selectively couplable to the first vacuum chamber to apply suction to the first port to draw target tissue through the first port into the first vacuum chamber.

8. The device of claim 7, wherein the source of negative fluid pressure includes a plunger slidably mounted within the first vacuum chamber so that, drawing the plunger proximally through the first vacuum chamber draws negative pressure in the first vacuum chamber to apply suction to the first port.

9. The device of claim 1, further comprising:
a radially protruding lip at the proximal end of the housing, extending along a surface that forms a portion of a sphere abutting the proximal end of the housing, wherein the lip has a diameter greater than that of the housing.

10. The device of claim 9, wherein the lip has a plurality of finger grips, the finger grips being concave cuts extending from the proximal end of the lip toward the distal end of the lip.

11. The device of claim 1, further comprising:
a proximally projecting handle, the handle extending proximally beyond the proximal end of the housing; and
an array of illuminating elements distributed around a circumference of the housing to enhance visualization of tissue.

12. The device of claim 11 wherein the illuminating elements are LEDs.

13. The device of claim 12, wherein the LEDs also include a secondary Narrow Band Imagining capability.

14. The device of claim 1, wherein the first ligation band holding structure includes a first port lip surrounding at least a portion of the first port.

15. The device of claim 14, wherein the tab of the first ligation band deploying mechanism is aligned with a gap in the first port lip so that movement of the tab through the gap will push a ligating band stretched around the lip off of the first ligation band holding structure.

16. The device of claim 1, wherein the tab is connected to a lever member connected to the housing so that pressure applied to the lever member moves the tab relative to the first ligation band holding structure to deploy a ligation band therefrom.

\* \* \* \* \*